US009402940B2

(12) United States Patent
Locke et al.

(10) Patent No.: US 9,402,940 B2
(45) Date of Patent: Aug. 2, 2016

(54) WOUND HEALING SYSTEM USING POSITIVE PRESSURE TO PROMOTE GRANULATION AT A TISSUE SITE

(71) Applicant: KCI Licensing, Inc., San Antonio, TX (US)

(72) Inventors: Christopher Brian Locke, Bournemouth (GB); Timothy Mark Robinson, Basingstoke (GB); Richard Daniel John Coulthard, Verwood (GB); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 14/597,024

(22) Filed: Jan. 14, 2015

(65) Prior Publication Data
US 2015/0190559 A1    Jul. 9, 2015

Related U.S. Application Data

(62) Division of application No. 13/473,986, filed on May 17, 2012, now Pat. No. 8,961,496.

(60) Provisional application No. 61/489,786, filed on May 25, 2011.

(51) Int. Cl.
*A61F 13/00* (2006.01)
*A61M 1/00* (2006.01)

(52) U.S. Cl.
CPC ........ *A61M 1/0088* (2013.01); *A61F 13/00068* (2013.01); *A61M 1/0066* (2013.01); *A61M 1/0084* (2013.01)

(58) Field of Classification Search
CPC ............ A61M 1/0001; A61M 1/0011; A61M 1/0017; A61F 13/00068
See application file for complete search history.

(56) References Cited

U.S. PATENT DOCUMENTS

| 1,355,846 | A | 10/1920 | Rannells |
|---|---|---|---|
| 2,547,758 | A | 4/1951 | Kelling |
| 2,632,443 | A | 3/1953 | Lesher |

(Continued)

FOREIGN PATENT DOCUMENTS

| AU | 550575 B2 | 3/1986 |
|---|---|---|
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.

(Continued)

*Primary Examiner* — Philip R Wiest
*Assistant Examiner* — Benjamin Klein

(57) ABSTRACT

A wound healing system for promoting healing of a wound of a patient includes a positive pressure source, a reduced pressure source, and a porous foam positioned in contact with the wound. The porous foam includes a plurality of flow channels in fluid communication with the reduced pressure source. The system further includes a filler member having a flexible wall defining an interior chamber. The interior chamber is in fluid communication with the positive pressure source, and a cover member is positioned over the filler member.

12 Claims, 11 Drawing Sheets

(56) References Cited

U.S. PATENT DOCUMENTS

| | | |
|---|---|---|
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0129660 A1 | 6/2007 | McLeod et al. |
| 2009/0254054 A1* | 10/2009 | Blott et al. .......... 604/290 |
| 2009/0306580 A1 | 12/2009 | Blott et al. |
| 2011/0054423 A1* | 3/2011 | Blott et al. .......... 604/319 |
| 2011/0112492 A1* | 5/2011 | Bharti et al. .......... 604/319 |
| 2012/0078154 A1* | 3/2012 | Pigg et al. .......... 602/46 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2004037334 A1 | 5/2004 |
| WO | 2005082435 A1 | 9/2005 |
| WO | 2009111657 A2 | 9/2009 |
| WO | 2009146441 A1 | 12/2009 |
| WO | 2010005709 A1 | 1/2010 |
| WO | 2010017437 A1 | 2/2010 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

(56) References Cited

OTHER PUBLICATIONS

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, p. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

European Search Report completed on Apr. 1, 2015 for EP Application No. 14195922.1.

* cited by examiner

WOUND HEALING SYSTEM USING POSITIVE PRESSURE TO PROMOTE GRANULATION AT A TISSUE SITE

RELATED APPLICATIONS

This application is a divisional of U.S. Non-Provisional patent application Ser. No. 13/473,986, entitled "Wound Healing System Using Positive Pressure to Promote Granulation at a Tissue Site," filed May 17, 2012, which claims the benefit, under 35 U.S.C §119(e), of the filing of U.S. Provisional Patent Application No. 61/489,786, entitled "Wound Healing System Using Positive Pressure to Promote Granulation at a Tissue Site," filed May 25, 2011. Each of the above applications are incorporated herein by reference for all purposes.

BACKGROUND OF THE INVENTION

1. Field of the Invention

The present invention relates generally to reduced pressure treatment systems and more particularly to a wound healing system for promoting granulation at a tissue site by delivery of reduced pressure and positive pressure.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced pressure source to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment.

SUMMARY

The problems presented by existing reduced pressure treatment systems are solved by the systems and methods of the illustrative embodiments described herein. In one illustrative embodiment, a wound healing system for promoting healing of a wound of a patient is provided. The system includes a positive pressure source, a reduced pressure source, and a porous foam positioned in contact with the wound. The porous foam includes a plurality of flow channels in fluid communication with the reduced pressure source. The system further includes a filler member having a flexible wall defining an interior chamber. The interior chamber is in fluid communication with the positive pressure source, and a cover member is positioned over the filler member.

In another embodiment, a wound healing system for promoting healing of a wound includes a positive pressure source, a reduced pressure source, and a filler member having an expandable wall defining an interior chamber. The interior chamber is in fluid communication with the positive pressure source, and a cover member is positioned over the filler member to secure the filler member at the wound. The cover member creates a sealed space capable of maintaining a reduced pressure, and the sealed spaced is in fluid communication with the reduced pressure source. In this embodiment, external fluids are not supplied to the wound.

In still another embodiment, a wound healing system for promoting healing of a wound of a patient includes a pump having an inlet and an exhaust. The inlet of the pump has a reduced pressure that is less than a reference pressure, and the exhaust has a positive pressure that is greater than the reference pressure. The system further includes a granulation-promoting material positioned at the wound and fluidly connected to the inlet of the pump. A filler member having an interior chamber is fluidly connected to the exhaust of the pump, and a cover member is positioned over the filler member to secure the filler member at the wound.

In yet another embodiment, a wound healing system for promoting healing of a wound of a patient includes a reduced pressure source and a filler member having a plurality of sealed compartments. Each of the sealed compartments includes a fluid at a pressure that is greater than or equal to an ambient pressure surrounding the sealed compartments. A cover member is positioned over the filler member to secure the filler member at the wound, the cover member creating a sealed space capable of maintaining a reduced pressure. The sealed spaced is in fluid communication with the reduced pressure source. The cover member provides a biasing force to the filler member directed toward the wound.

Other objects, features, and advantages of the illustrative embodiments will become apparent with reference to the drawings and detailed description that follow.

DETAILED DESCRIPTION OF ILLUSTRATIVE EMBODIMENTS

Figure 1:
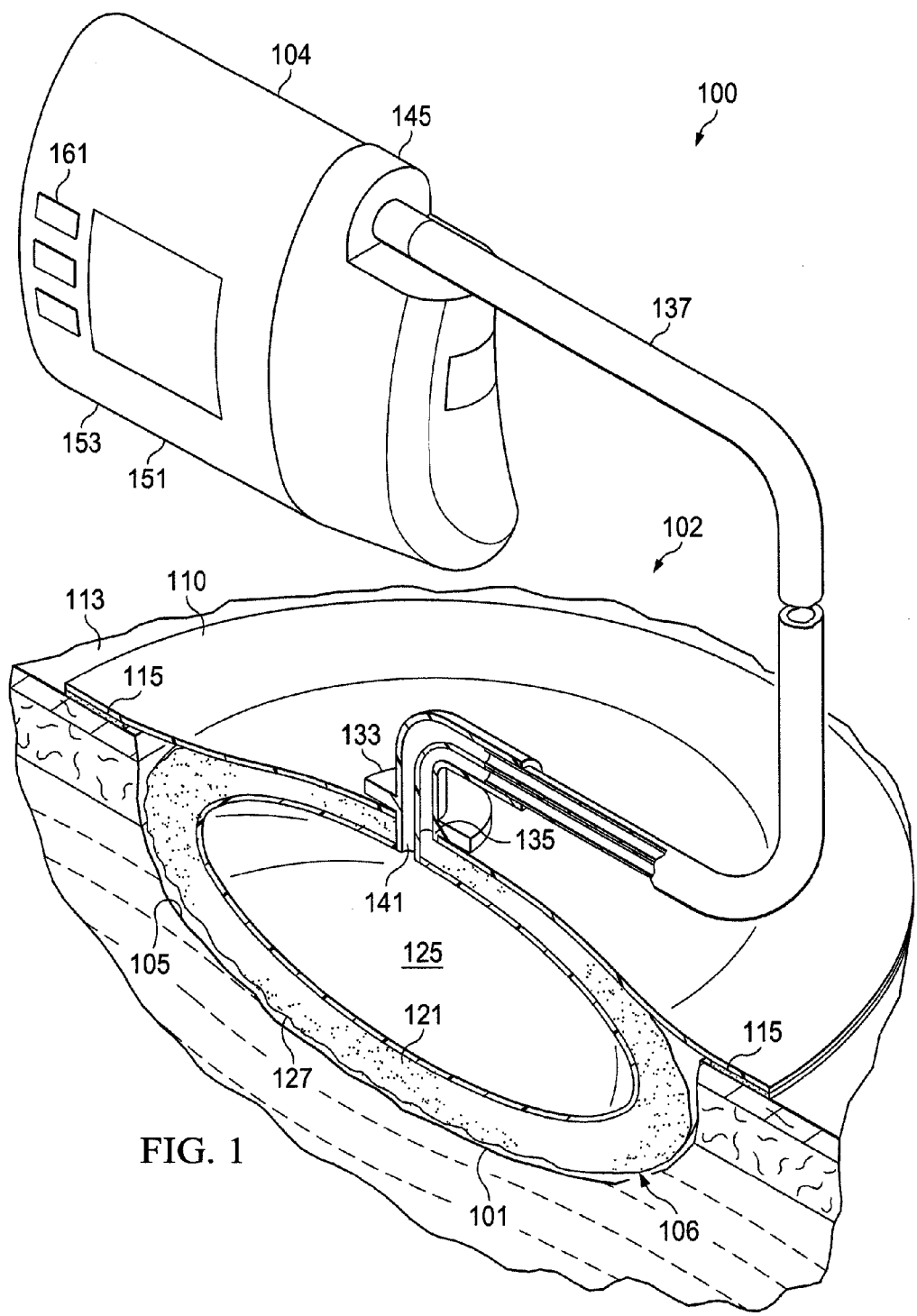
FIG. 1 illustrates a partially cross-sectional, perspective view of a tissue treatment system according to an illustrative embodiment.

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "positive pressure" as used herein generally refers to a pressure greater than the ambient pressure at a tissue site that is being subjected to treatment. In some cases, this positive pressure will be greater than the atmospheric pressure at which the patient is located. Alternatively, the positive pressure may be greater than a hydrostatic pressure associated with tissue at the tissue site.

The tissue treatment systems and methods described in this application improve the treatment of a tissue site by increasing or improving granulation tissue development, thus allowing healing of a wound that may not otherwise heal with traditional treatment modalities, or in some cases, allowing an increased rate in healing of a wound. Granulation may be promoted by exposing the tissue site to micro-mechanical stresses and strains. While the creation of micro-mechanical stresses and strains at a tissue site may be provided by applying a reduced pressure to a sealed space adjacent the tissue site, the system and methods described herein employ the use of positive pressure or forces to create such stresses and strains. Use of positive pressure or forces can decrease the amount of reduced pressure that is applied to a tissue site to remove fluids and exudate from the tissue site. In some cases, use of a positive pressure or forces may eliminate the need for reduced pressure entirely, especially when absorbent materials or other fluid-removal materials or mechanisms are employed.

Referring to FIG. 1, an illustrative embodiment of a tissue treatment system 100 for treating a tissue site 101 on a patient includes a dressing 102 placed proximate to the tissue site 101 and a therapy unit 104 fluidly coupled to the dressing 102. As used herein, the term "tissue site" may refer to a wound, such as a wound 105, or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The dressing 102 is configured to promote the growth of new tissue at the tissue site 101 and includes a wound healing apparatus 106 positioned adjacent to or, in some embodiments, in contact with the tissue site 101. The dressing 102 may further include a cover or drape 110 positioned over the wound healing apparatus 106 to secure the wound healing apparatus 106 at the tissue site 101 and to seal a space that is located beneath the cover and is at least partially occupied by the wound healing apparatus 106. In one embodiment, the drape 110 extends beyond a perimeter of the tissue site 101 and is placed either in contact with or otherwise in proximity to a patient's epidermis 113 to create a fluid seal between the drape 110 and the epidermis 113. The drape 110 may include an adhesive 115 or bonding agent to secure the drape 110 to the epidermis 113. In one embodiment, the adhesive 115 may be used to create a seal between the drape 110 and the epidermis 113 to prevent leakage of reduced pressure from the tissue site 101. In another embodiment, a seal layer (not shown) such as, for example, a hydrogel or other material may be disposed between the drape 110 and the epidermis 113 to augment or substitute for the sealing properties of the adhesive 115. As used herein, "fluid seal" means a seal adequate to maintain reduced pressure at a desired site given the particular reduced pressure source involved and the particular treatment desired. In one embodiment, the drape 110 and the bonding characteristics of the drape 110 provide sealing sufficient to prevent leakage greater than 0.5 L/min at 125 mmHg reduced pressure.

The wound healing apparatus 106 may include a manifold 121 and a filler member 125. The term "manifold" as used herein generally refers to a substance or structure that is provided to assist in applying reduced pressure to, delivering fluids to, or removing fluids from the tissue site 101. The manifold typically includes a plurality of flow channels or pathways that distribute fluids provided to and removed from the tissue site around the manifold. In one illustrative embodiment, the flow channels or pathways are interconnected to improve distribution of fluids provided or removed from the tissue site 101. Examples of manifolds may include, for example, without limitation, devices that have structural elements arranged to form flow channels, such as, for example, cellular foam, open-cell foam, porous tissue collections, liquids, gels, and foams that include, or cure to include, flow channels. In one embodiment, the wound healing apparatus 106 includes a porous foam and having a plurality of interconnected cells or pores that act as flow channels. The porous foam may be a polyurethane, open-cell, reticulated foam such as GranuFoam® material manufactured by Kinetic Concepts, Incorporated of San Antonio, Tex.

The filler member 125 of the reduced pressure apparatus 106 may be provided to occupy additional space or volume between the tissue site 101 and the cover 110 and may also be provided to better facilitate the application of a positive force to the tissue site 106 in order to encourage granulation and new tissue growth. The filler member 125 may in some embodiments be an inflatable bladder or balloon that is expandable when injected or otherwise filled with a fluid. In other embodiments, the filler member 125 may be a pre-filled bladder or other container that is positioned between the tissue site 106 and the cover 110. Several examples of filler members 125 are provided herein.

The manifold 121 and filler member 125 may work together to encourage tissue growth in the presence of a positive force or pressure. In one-embodiment, the manifold 121 may include at least one granulation-promoting surface 127 that is capable of contacting the tissue site 101. The granulation-promoting surface 127 is capable of inducing micro-stresses and micro-strain at the tissue site 101 when the granulation-promoting surface 127 contacts the tissue site 101. For example, if the manifold 121 is a reticulated porous foam that includes a plurality of interconnected cells formed by struts or cell walls, the struts of the reticulated foam may be capable of inducing micro-stresses and micro-strains when the struts are pressed against or into the tissue. By sealing the manifold 121 and filler member 125 proximate the tissue site 101 with the cover 110, expansion of the filler member 125 within the sealed space beneath the cover 110 directs a force on the manifold 121 at least in the direction of the tissue site 101. This force is capable of generating the required micro-stresses and micro-strains where the tissue contacts the granulation-promoting surface 127.

In FIG. 1, the filler member 125 is embedded within the manifold such that the manifold completely surrounds the filler member 125. As described in more detail below, other arrangements of manifolds and filler members may be used, and many variations of both the manifold and filler member are possible. In one embodiment, the manifold may be omitted and the filler member alone positioned within the sealed space beneath the cover. In this embodiment, the filler member may include a granulation-promoting surface that is placed in contact with the tissue site. The granulation-promoting surface may includes projections, protrusions, or a substantially-rough profile to induce micro-stresses and micro-strains at the tissue site. In still other embodiments, the filler member may be omitted and simply a manifold or other granulation-inducing substrate may be placed beneath the cover. In this embodiment, a force on the manifold or granulation-inducing substrate may create the desired micro-strain to induce granulation at the tissue site.

Referring still to FIG. 1, the dressing 102 further may include a pressure interface 133 fluidly coupled to the wound healing apparatus 106 and the cover 110. In one embodiment, the interface 133 may be positioned adjacent to or coupled to the cover 110 to provide fluid access to the wound healing apparatus 106. The drape 110 includes an aperture 135 for providing fluid access to the interface 133. A conduit 137 fluidly couples the therapy unit 104 and the interface 133. The interface 133 is capable of allowing reduced pressure to be delivered to the tissue site 101 when it is desired to remove fluid from the tissue site 101 under the influence of reduced pressure. The interface 133 may also be fluidly coupled to the filler member 125 through a filler conduit 141. Fluid connection between the interface 133 and the filler member 125 allows a fluid (i.e. a gas or liquid) to be delivered to the filler member 125 under positive pressure such that the filler member 125 may be inflated or expanded.

In one embodiment, the therapy unit 104 includes a fluid containment member 145 in fluid communication with a reduced pressure source 151. In the embodiment illustrated in FIG. 1, the fluid containment member 145 is a collection canister that includes a chamber for collecting fluids from the tissue site 101. The fluid containment member 145 alternatively could be an absorbent material or any other container, device, or material that is capable of collecting fluid.

A separate positive pressure source 153 may be housed within the therapy unit 104. Alternatively, a singe vacuum pump may be disposed within the therapy unit 104 such that an inlet of the vacuum pump serves as the reduced pressure source 151 and an outlet of the vacuum pump serves as the positive pressure source 153. The conduit 137 may be a multi-lumen tube that is capable of providing one or more conduits to deliver reduced pressure to the dressing 102 and one or more conduits to deliver positive pressure to the dressing 102. Liquids or exudates communicated from the wound healing apparatus 106 through the conduit 137 are removed from the conduit 137 and retained within the collection canister 145. Additional information regarding the transfer of fluids between the dressing and the therapy unit is provided below with reference to FIG. 2.

Referring still to FIG. 1, the reduced pressure source 151 and positive pressure source 153 may be one or more electrically-driven vacuum pumps. In another implementation, the reduced and positive pressure sources 151, 153 may instead be one or more manually-actuated or manually—charged pumps that do not require electrical power. In one embodiment, the reduced pressure and positive pressure sources 151, 153 may be one or more piezoelectric-actuated micropumps that may be positioned remotely from the dressing 102, or at the dressing beneath or adjacent to the cover 110. The reduced and positive pressure sources 151, 153 instead may be any other type of pump, or alternatively a wall suction port or air delivery port such as those available in hospitals and other medical facilities. The reduced and positive pressure sources 151, 153 may be housed within or used in conjunction with the therapy unit 104, which may also contain sensors, processing units, alarm indicators, memory, databases, software, display units, and user interfaces 161 that further facilitate the application of reduced pressure treatment to the tissue site 101. In one example, pressure-detection sensors (not shown) may be disposed at or near the reduced and positive pressure sources 151, 153. The pressure-detection sensors may receive pressure data from the interface 133 via lumens in the conduit 137 that are dedicated to delivering reduced pressure data to the pressure-detection sensors. The pressure-detection sensors may communicate with a processing unit that monitors and controls the reduced pressure and positive pressure that is delivered by the reduced and positive pressure sources 151, 153.

Figure 2:
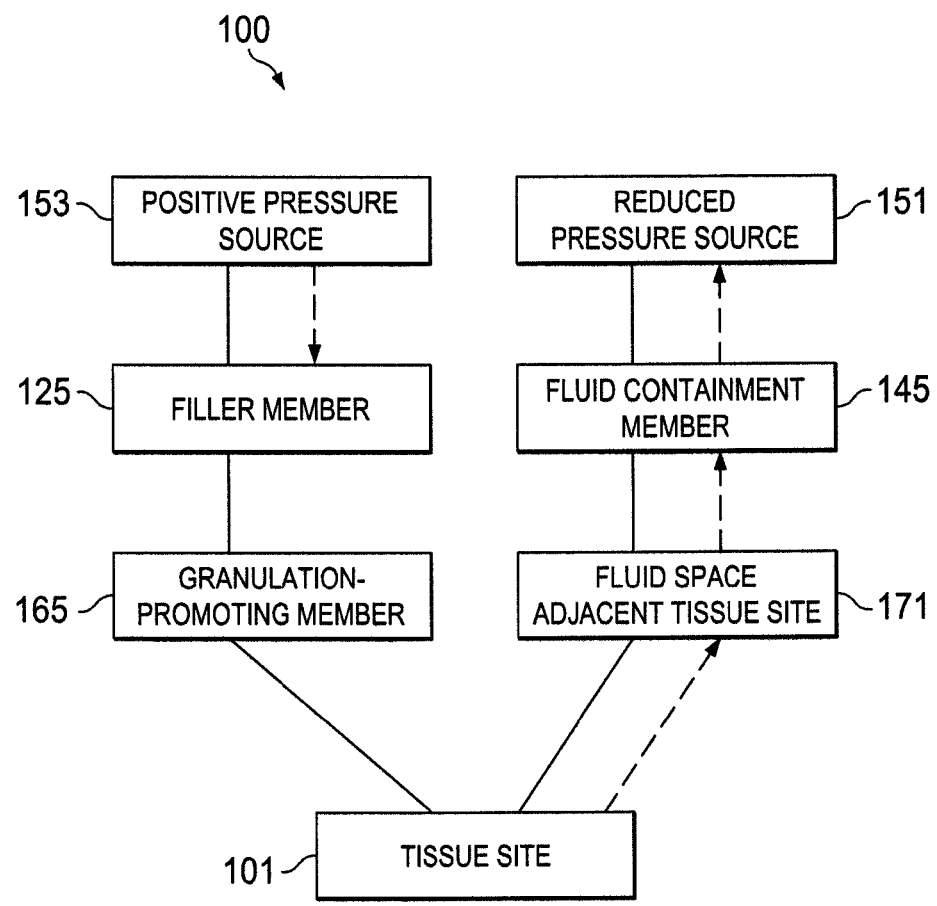
FIG. 2 illustrates a fluid flow schematic for an embodiment of the tissue treatment system of FIG. 1.

Referring to FIG. 2, a fluid flow schematic is depicted for an embodiment of the tissue treatment system 100. Dashed lines between system components in FIG. 2 represent the flow of fluids between those components. Solid lines represent physical connections or proximities that may exist between the components. As depicted in FIG. 2, the positive pressure source 153 provides a fluid such as a gas or a liquid to the filler member 125. The direction of fluid flow is from the positive pressure source 153 to the filler member 125. The positive pressure source 153 may be physically (and fluidly) connected to the filler member 125 by a conduit such as conduit 137 (see FIG. 1), or alternatively the positive pressure source 153 may include an outlet directly coupled to the filler member 125. In one embodiment, the positive pressure source 153 may be a micropump such as a piezoelectric-actuated pump that is disposed adjacent to the filler member 125. The filler member 125 is operably associated with a granulation-promoting member 165 that may be placed adjacent to or in contact with the tissue site 101. The granulation-promoting member may be a manifold such as manifold 121, a granulation-promoting surface on the filler member 125, or any other type of material or substrate that is capable of promoting granulation tissue growth.

The reduced pressure source 151 provides reduced pressure by drawing or pulling a fluid such as a gas or a liquid toward the reduced pressure source 151. In one embodiment, the reduced pressure source 151 is physically (and fluidly) connected to the fluid containment member 145 and draws fluid from the fluid containment member 145. The reduced pressure created at the reduced pressure source 151 and the fluid containment member 145 is capable of drawing fluid from a fluid space 171 adjacent the tissue site 101. It should be understood that the fluid space 171 may be occupied by the manifold 121 to better distribute reduced pressure within the fluid space 171 and at the tissue site 101, thereby resulting in more efficient removal of the fluid.

Figure 3A:
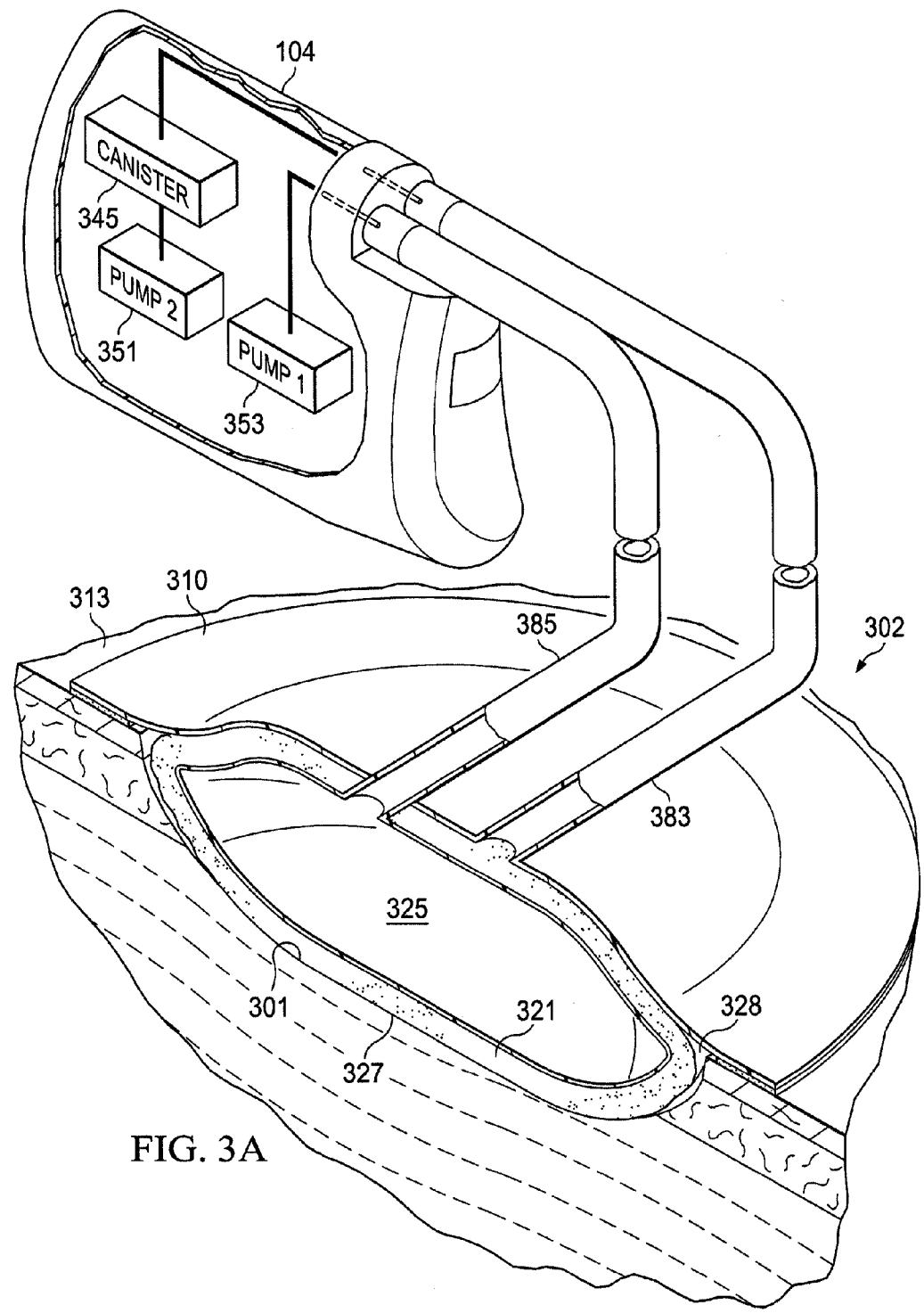
FIGS. 3A and 3B illustrate a partially cross-sectional, perspective view of a tissue treatment system according to an illustrative embodiment.
Figure 3B:
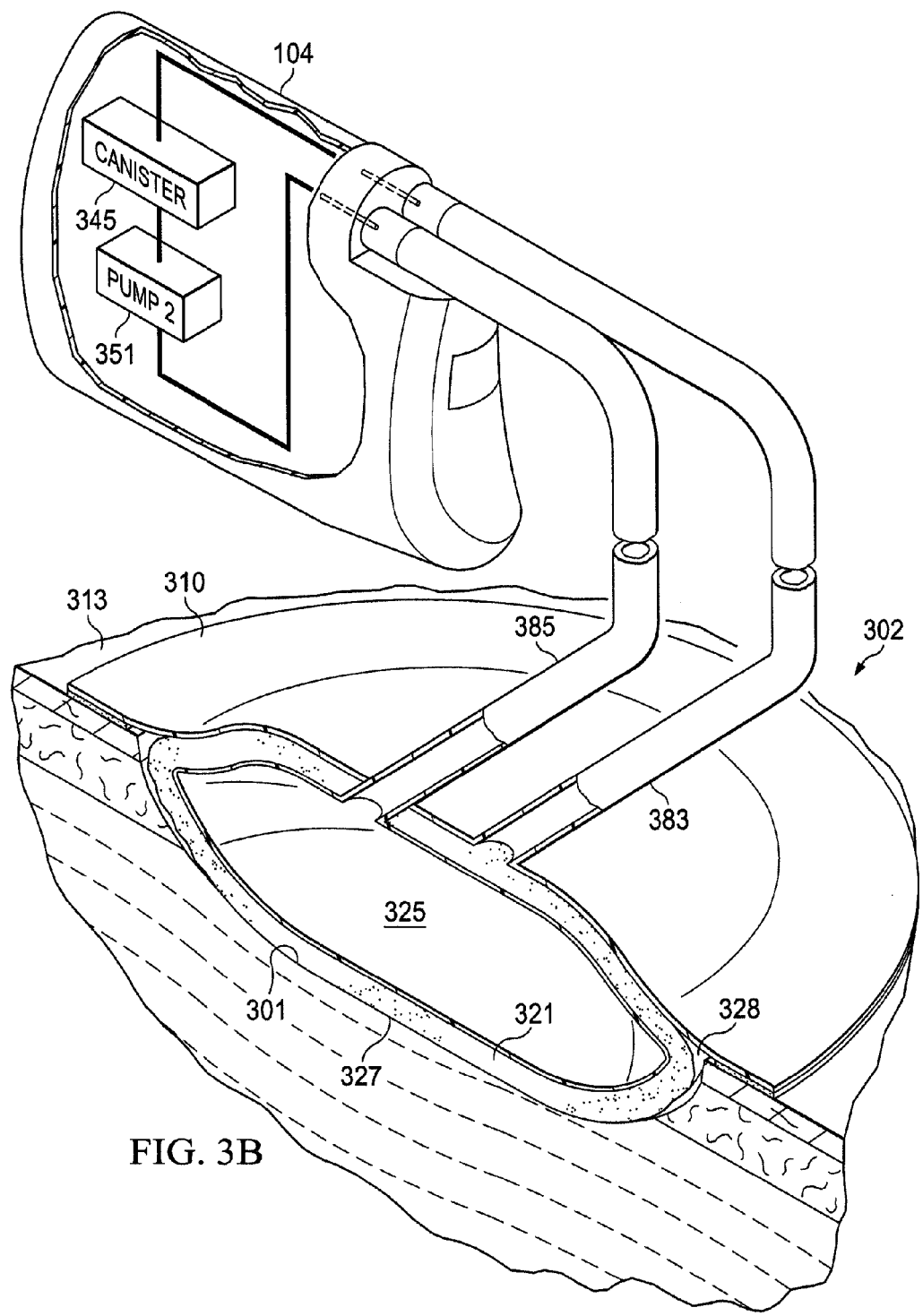

Referring to FIGS. 3A and 3B, an illustrative embodiment of a tissue treatment system 300 for treating a tissue site 301 on a patient includes a dressing 302 placed proximate to the tissue site 301 and a therapy unit 104 fluidly coupled to the dressing 302. Tissue treatment system 300 is similar to tissue treatment system 100 and includes many components that are the same as or similar to those in tissue treatment system 100. Tissue treatment system 300 illustrates a filler member 325 that is fully inflated with a fluid. The filler member 125 is embedded within a manifold 321 that includes at least one granulation-promoting surface 327 that is brought into contact with the tissue site 301 by the inflation of the filler member 325. The filler member 325 and manifold 321 are constrained by a cover 310 secured to an epidermis 313 of the patient such that biasing forces may be applied to the tissue site 301 by the granulation-promoting surface 327. While the cover 310 may be substantially inelastic such that the cover 310 acts as a substantially rigid constraint, the cover 310 may instead by elastic, thereby allowing some expansion of the dressing above the epidermis 313 of the patient that surrounds the tissue site 301 (as shown in FIGS. 3A and 3B). The cover 310 creates a sealed space 328 beneath the cover 310 in which the manifold 321 and the filler member 325 reside.

In one embodiment, an inner space of the filler member 325 is fluidly coupled to a positive pressure source 353, while a reduced pressure source 351 is fluid coupled to the manifold 321. In the embodiment illustrated in FIG. 3A, the positive pressure source 353 and the reduced pressure source 351 are each separate pumps. In FIG. 3B, the positive pressure source 353 and the reduced pressure source 351 are the same pump, the pump providing reduced pressure to the manifold 321 through an inlet of the pump and positive pressure to the filler member 325 through the outlet of the pump. While pumps are illustrated as being the positive pressure source 353 and reduced pressure source 351 in FIGS. 3A and 3B, it should be noted that the positive and reduced pressure sources 353, 351 may be any source of positive or negative fluid flow as described previously with respect to positive pressure source 153 and reduced pressure source 151.

In the embodiments illustrated in FIGS. 3A and 3B, fluids are exchanged with the manifold 321 and the filler member 325 through conduits 383, 385. Conduit 383 permits the application of reduced pressure and thus the removal of fluids from the manifold 321 or the space 328 surrounding the filler member 325. Conduit 385 permits the application of positive pressure and thus the delivery of fluids to the filler member 325. Conduits 383, 385 may be any type of tube or other fluid conveying device. As illustrated in FIGS. 3A and 3B, conduits 383, 385 may be positioned through the cover 310. In this embodiment, it is preferred that an aperture in the cover 310 though which each conduit 383, 385 is placed be sealed around the conduit 383, 385, either using a sealant or other adhesive, or using a drape material that may be adhered to both the cover 310 and the conduit 383, 385. Alternatively, the conduits 383, 385 may be inserted beneath the cover 310 near an edge of the cover 310 where the cover 310 is adhered to the patient's epidermis 313. Again, sealing of the cover 310 around the conduit 383, 385 entry point is important, both to maintain the ability of the cover 310 to secure the filler member 325 and the manifold 321 at the tissue site 301 and to allow the cover 310 to maintain a reduced pressure within the manifold 321 or the space 328 between the filler member 325 and the tissue site 301. Similarly, it is important for conduit 385 to be properly sealed to the filler member 325. Proper sealing of the conduit 385 prevents positively-pressurized fluid from the conduit 385 from leaking into the manifold 325 or the space 328 between the filler member 325 and the tissue site 301. While the conduits 383, 385 have been described as passing through or underneath the cover 310, the conduits 383, 385 instead could be connected to an interface similar to interface 133 associated with FIG. 1. The interface would allow sealed passage of fluid carried by the conduits 383, 385 through the cover 310.

A canister 345 may be fluidly coupled between the dressing 302 and the reduced pressure source 351. The canister 345 is capable of collecting fluids (especially liquids) drawn from the tissue site 301 by the reduced pressure source 351.

Figure 4:
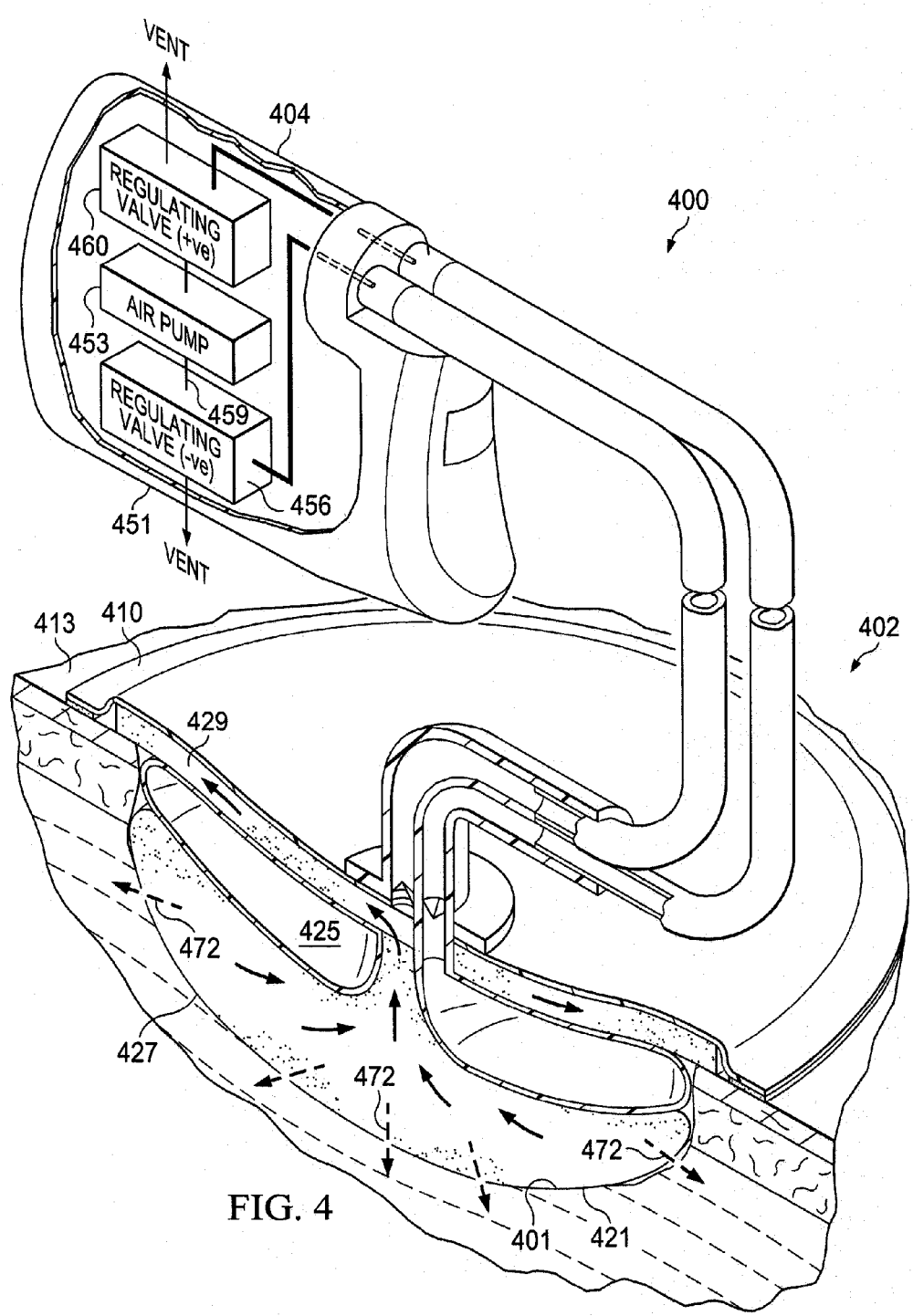
FIG. 4 illustrates a partially cross-sectional, perspective view of a tissue treatment system according to an illustrative embodiment.

Referring to FIG. 4, an illustrative embodiment of a tissue treatment system 400 for treating a tissue site 401 on a patient includes a dressing 402 placed proximate to the tissue site 401 and a therapy unit 404 fluidly coupled to the dressing 402. Tissue treatment system 400 is similar to tissue treatment systems 100, 300 and includes many components that are the same as or similar to those in tissue treatment systems 100, 300.

Tissue treatment system 400 includes a filler member 425 that is inflated with a fluid. Positioned beneath the filler member 425 is a manifold 421 that includes at least one granulation-promoting surface 427 that is brought into contact with the tissue site 401 by the inflation of the filler member 425. An absorbent layer 429 is positioned above the filler member 425 and in fluid communication with the manifold 421. The absorbent layer 429, filler member 425, and manifold 421 are constrained by a cover 410 secured to an epidermis 413 of the patient. The attachment of the cover 410 over the layers of the dressing 402 allows biasing forces to be applied to the tissue site 401 by the granulation-promoting surface 427. While the cover 410 may be substantially inelastic such that the cover 410 acts as a substantially rigid constraint, the cover 410 instead may be elastic, thereby allowing some expansion of the dressing above or below the epidermis 413 of the patient that surrounds the tissue site 401.

In one embodiment, an inner space of the filler member 425 is fluidly coupled to a positive pressure source 453, while a reduced pressure source 451 is fluid coupled to the absorbent layer 429 and the manifold 421. In the embodiment illustrated in FIG. 4, the function of the positive pressure source 453 and the reduced pressure source 451 are provided by a single pump. Reduced pressure is provided by an inlet 454 of the pump and is regulated by a regulating valve 456. Positive pressure is provided by an outlet 458 of the pump and is regulated by a regulating valve 460. While a single pump is illustrated as providing both positive and negative pressure, it should be noted that the positive and reduced pressures may be supplied by separate pumps or by any other source of positive or negative fluid flow.

The fluid connection between the reduced pressure source 451 and the absorbent layer 429 assists in drawing liquids from the manifold 421 into the absorbent layer 429 for storage. The absorbent layer 451 may be formed from an absorbent, adsorbent, desiccant, or any other type of material that is capable of capturing or storing liquid from the tissue site 401. Examples of materials from which the absorbent layer may be constructed include, without limitation, BASF's Luquafleece material, superabsorbent-fibre-based non-woven materials such as that offered by Technical Absorbents, hydrophilic foams such as that offered by Foam Partners HME, high-wicking fibre-based materials such as that offered by Filtrona, and hydrophylic sintered polymers such as that offered by Poryair.

As illustrated in FIG. 4, the application of reduced pressure through the absorbent layer 429 and manifold 421 may result in the dressing 402 being compressed such that cover 410 is pulled below the epidermis 413 of the patient that surrounds the tissue site 401. While this compression of the dressing 402 assists in applying a biasing force, represented by arrows 472, to the tissue site 401, the biasing force may be increased by the presence of the filler member 425 beneath the cover 410. The inflation of the filler member 425 beneath the cover 410 results in less reduced pressure being needed to encourage granulation. Instead, reduced pressure can be provided primarily to remove fluid from the tissue site 401.

Figure 5:
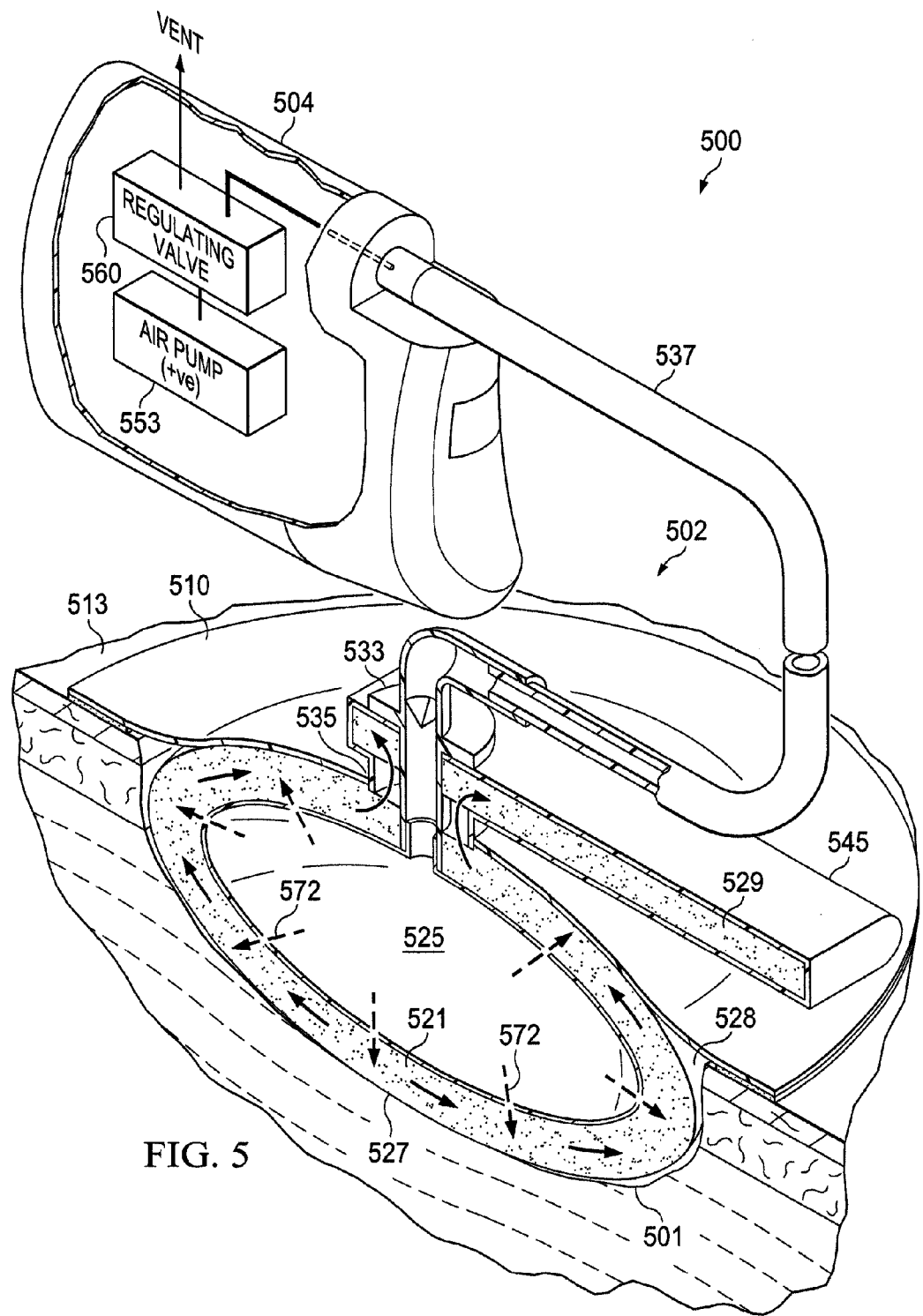
FIG. 5 illustrates a partially cross-sectional, perspective view of a tissue treatment system according to an illustrative embodiment.

Referring to FIG. 5, an illustrative embodiment of a tissue treatment system 500 for treating a tissue site 501 on a patient includes a dressing 502 placed proximate to the tissue site 501 and a therapy unit 504 fluidly coupled to the dressing 502. Tissue treatment system 500 is similar to tissue treatment systems 100, 300, 400 and includes many components that are the same as or similar to those in tissue treatment systems 100, 300, 400.

Tissue treatment system 500 includes a filler member 525 that is inflated with a fluid. The filler member 525 is embedded within a manifold 521 that includes at least one granulation-promoting surface 527 that is brought into contact with the tissue site 501 by the inflation of the filler member 525. The filler member 525 and manifold 521 are constrained by a cover 510 secured to an epidermis 513 of the patient such that biasing forces may be applied to the tissue site 501 by the granulation-promoting surface 527. The cover 510 creates a sealed space 528 beneath the cover 510 in which the manifold 521 and filler member 525 reside. While the cover 510 may be substantially inelastic such that the cover 510 acts as a substantially rigid constraint, the cover 510 instead may be elastic, thereby allowing some expansion of the dressing above or below the epidermis 513 of the patient that surrounds the tissue site 501.

A fluid containment member 545 is positioned in fluid communication with the manifold 521 and the space 528 beneath the cover 510. In one embodiment, the fluid containment member 545 is a fluid pouch that includes an absorbent 529 similar to other absorbents described herein. The fluid containment member 545 may be positioned above the cover 510 outside of the sealed space 528. Alternatively, the fluid containment member 545 may be positioned beneath the cover, and in one embodiment fluid containment member 545, or the absorbent 529 therein, may be in direct contact with the manifold 521.

In the embodiment illustrated in FIG. 5, an inner space of the filler member 525 is fluidly coupled to a positive pressure source 553. The pressure of fluid provided by the positive pressure source 553 is regulated by a regulating valve 560. No reduced pressure source is provided in the embodiment illustrated in FIG. 5. Instead fluid removal from the tissue site 501 is provided by the fluid containment member 545. As the manifold 521 becomes filled with fluid, the absorbent 529 in the fluid containment member 545 assists in drawing the fluid from the manifold 521 and into the fluid containment member 545 for storage. The movement of the fluid is further aided by the inflation of the filler member 525, which decreases the volume of the space 528 occupied by the manifold 521 and thus the fluid.

While no reduced pressure source is illustrated in FIG. 5, it is important to note that a reduced pressure source may be fluidly connected to the fluid containment member 545 to provide active drainage of the space 528 and the tissue site 501. Such a reduced pressure source may be similar to the other reduced pressure sources described herein.

In FIG. 5, the fluid containment member 545 is fluidly connected to the manifold 521 by a pressure interface 533 positioned adjacent to or coupled to the cover 510. The cover 510 includes an aperture 535 through which the pressure interface 533 passes. A conduit 537 fluidly couples the therapy unit 504 (and positive pressure source 553) to the interface 533. Fluid connection between the interface 533 and the filler member 525 allows a fluid (i.e. a gas or liquid) to be delivered to the filler member 525 under positive pressure such that the filler member 525 may be inflated or expanded.

As illustrated in FIG. 5, the filling of the filler member 525 in the absence of reduced pressure to the space 528 may result in the dressing 502 expanding above the epidermis 513 of the patient that surrounds the tissue site 501. This expansion of the dressing 502 assists in applying a biasing force, represented by arrows 572, to the tissue site 501. The inflation of the filler member 525 beneath the cover 510 results in no reduced pressure being needed to encourage granulation. In this particular embodiment, fluid is removed from the dressing 502 without reduced pressure as well.

Figure 6:
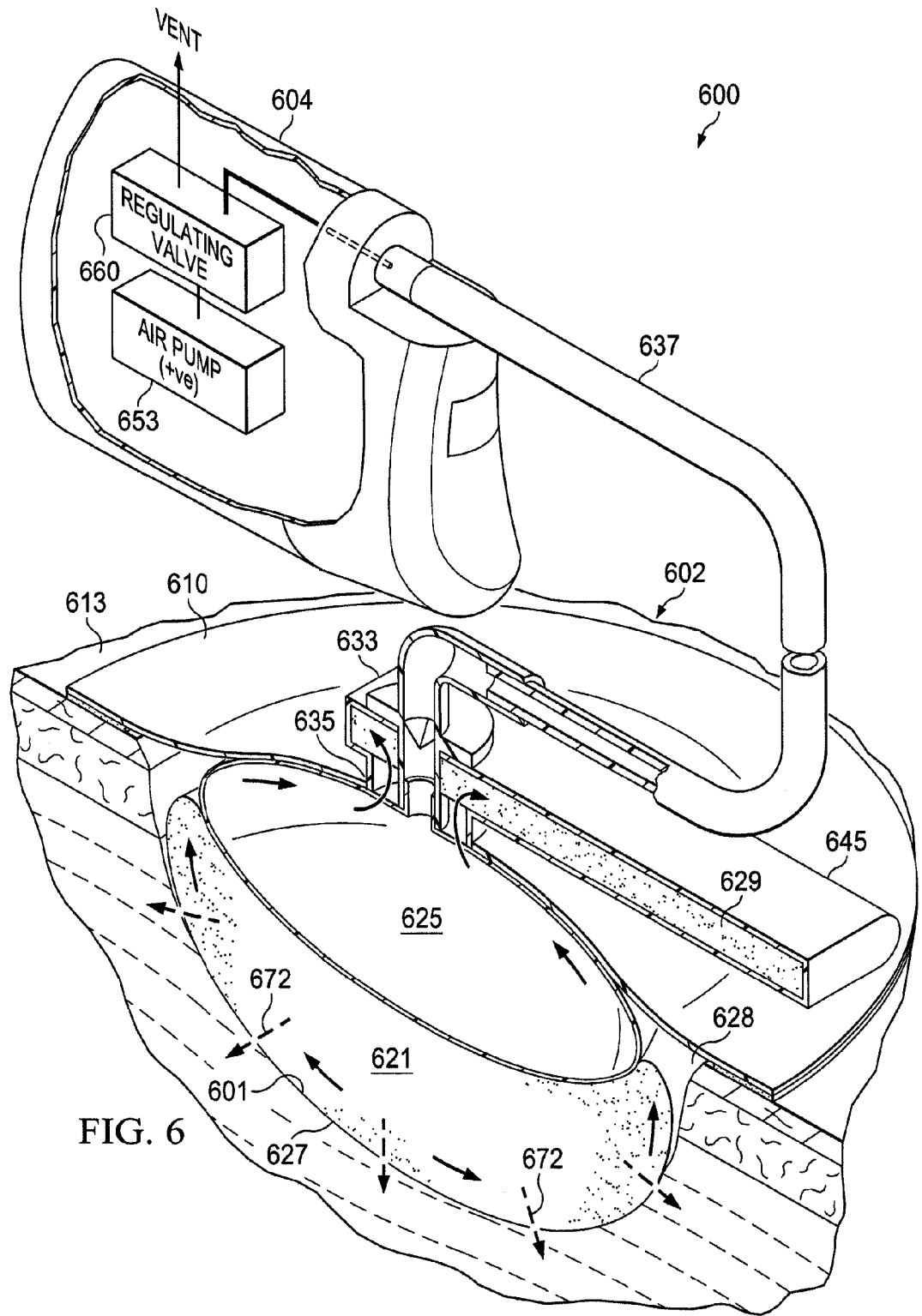
FIG. 6 illustrates a partially cross-sectional, perspective view of a tissue treatment system according to an illustrative embodiment.

Referring to FIG. 6, an illustrative embodiment of a tissue treatment system 600 for treating a tissue site 601 on a patient includes a dressing 602 placed proximate to the tissue site 601 and a therapy unit 604 fluidly coupled to the dressing 602. Tissue treatment system 600 is similar to tissue treatment systems 100, 300, 400, 500 and includes many components that are the same as or similar to those in tissue treatment systems 100, 300, 400, 500.

Tissue treatment system 600 includes a filler member 625 that is inflated with a fluid. Positioned beneath the filler member 625 is a manifold 621 that includes at least one granulation-promoting surface 627 that is brought into contact with the tissue site 601 by the inflation of the filler member 625. The filler member 625 and manifold 621 are constrained by a cover 610 secured to an epidermis 613 of the patient such that biasing forces may be applied to the tissue site 601 by the granulation-promoting surface 627. The cover creates a sealed space 628 beneath the cover in which the manifold 621 and filler member 625 reside. While the cover 610 may be substantially inelastic such that the cover 610 acts as a substantially rigid constraint, the cover 610 instead may be elastic, thereby allowing some expansion of the dressing above or below the epidermis 613 of the patient that surrounds the tissue site 601.

A fluid containment member 645 is positioned in fluid communication with the manifold 621 and the space 628 beneath the cover 610. In one embodiment, the fluid containment member 645 is a fluid pouch that includes an absorbent 629 similar to other absorbents described herein. The fluid containment member 645 may be positioned above the cover 610 outside of the sealed space 628. Alternatively, the fluid containment member 645 may be positioned beneath the cover, and in one embodiment fluid containment member 645, or absorbent 629 therein, may be in direct contact with the manifold 621.

In the embodiment illustrated in FIG. 6, an inner space of the filler member 625 is fluidly coupled to a positive pressure source 653. The pressure of fluid provided by the positive pressure source 653 is regulated by a regulating valve 660. No reduced pressure source is provided in the embodiment illustrated in FIG. 6. Instead fluid removal from the tissue site 601 is provided by the fluid containment member 645. As the manifold 621 becomes filled with fluid, the absorbent 629 in the fluid containment member 645 assists in drawing the fluid from the manifold 621 and into the fluid containment member 645 for storage. The movement of the fluid is further aided by the inflation of the filler member 625, which decreases the volume of the space 628 occupied by the manifold 621 and thus the fluid.

While no reduced pressure source is illustrated in FIG. 6, it is important to note that a reduced pressure source may be fluidly connected to the fluid containment member 645 to provide active drainage of the space 628 and the tissue site 601. Such a reduced pressure source may be similar to the other reduced pressure sources described herein.

In FIG. 6, the fluid containment member 645 is fluidly connected to the manifold 621 by a pressure interface 633 positioned adjacent to or coupled to the cover 610. The cover 610 includes an aperture 635 through which the pressure interface 633 passes. A conduit 637 fluidly couples the therapy unit 604 (and positive pressure source 653) to the interface 633. Fluid connection between the interface 633 and the filler member 625 allows a fluid (i.e. a gas or liquid) to be delivered to the filler member 625 under positive pressure such that the filler member 625 may be inflated or expanded.

As illustrated in FIG. 6, the filling of the filler member 625 in the absence of reduced pressure to the space 628 may result in the dressing 602 expanding above the epidermis 613 of the patient that surrounds the tissue site 601. This expansion of the dressing 602 assists in applying a biasing force, represented by arrows 672, to the tissue site 601. The inflation of the filler member 625 beneath the cover 610 results in no reduced pressure being needed to encourage granulation. In this particular embodiment, fluid is removed from the dressing 602 without reduced pressure as well.

Figure 7:
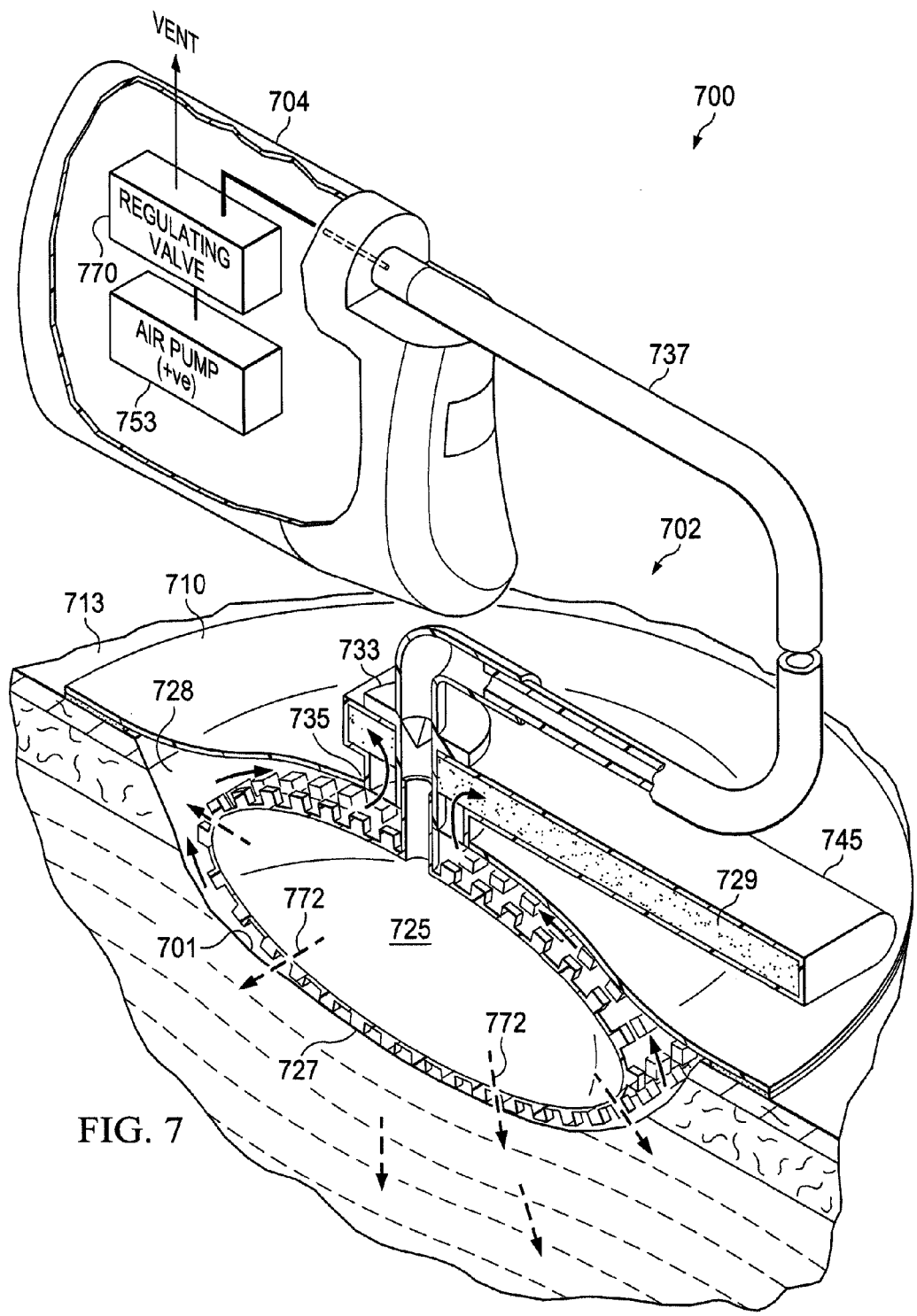
FIG. 7 illustrates a partially cross-sectional, perspective view of a tissue treatment system according to an illustrative embodiment.

Referring to FIG. 7, an illustrative embodiment of a tissue treatment system 700 for treating a tissue site 701 on a patient includes a dressing 702 placed proximate to the tissue site 701 and a therapy unit 704 fluidly coupled to the dressing 702. Tissue treatment system 700 is similar to tissue treatment systems 100, 300, 400, 500, 600 and includes many components that are the same as or similar to those in tissue treatment systems 100, 300, 400, 500, 600.

Tissue treatment system 700 includes a filler member 725 that is inflated with a fluid. Unlike, some previously illustrated embodiments, the embodiment illustrated in FIG. 7 does not include a manifold. Instead, the filler member 725 includes at least one granulation-promoting surface 727 that is brought into contact with the tissue site 701 when the filler member 725 is inflated. The filler member 725 is constrained by a cover 710 secured to an epidermis 713 of the patient such that biasing forces may be applied to the tissue site 701 by the granulation-promoting surface 727. The cover creates a sealed space 728 beneath the cover in which the filler member 725 resides. While the cover 710 may be substantially inelastic such that the cover 710 acts as a substantially rigid constraint, the cover 710 instead may be elastic, thereby allowing some expansion of the dressing above or below the epidermis 713 of the patient that surrounds the tissue site 701.

A fluid containment member 745 is positioned in fluid communication with the space 728 beneath the cover 710. In one embodiment, the fluid containment member 745 is a fluid pouch that includes an absorbent 729 similar to other absorbents described herein. The fluid containment member 745 may be positioned above the cover 710 outside of the sealed space 728. Alternatively, the fluid containment member 745 may be positioned beneath the cover, and in one embodiment fluid containment member 745, or absorbent 729 therein, may be in direct contact with the filler member 725.

In the embodiment illustrated in FIG. 7, an inner space of the filler member 725 is fluidly coupled to a positive pressure source 753. The pressure of fluid provided by the positive pressure source 753 is regulated by a regulating valve 770. No reduced pressure source is provided in the embodiment illustrated in FIG. 7. Instead fluid removal from the tissue site 701 is provided by the fluid containment member 745. As the space 728 becomes filled with fluid, the absorbent 729 in the fluid containment member 745 assists in drawing the fluid from the spaced 728 and into the fluid containment member 745 for storage. The movement of the fluid is further aided by the inflation of the filler member 725, which decreases the volume of the space 728.

While no reduced pressure source is illustrated in FIG. 7, it is important to note that a reduced pressure source may be fluidly connected to the fluid containment member 745 to provide active drainage of the space 728 and the tissue site 701. Such a reduced pressure source may be similar to the other reduced pressure sources described herein.

In FIG. 7, the fluid containment member 745 is fluidly connected to the space 728 by a pressure interface 733 positioned adjacent to or coupled to the cover 710. The cover 710 includes an aperture 735 through which the pressure interface 733 passes. A conduit 737 fluidly couples the therapy unit 704 (and positive pressure source 753) to the interface 733. Fluid connection between the interface 733 and the filler member 725 allows a fluid (i.e. a gas or liquid) to be delivered to the filler member 725 under positive pressure such that the filler member 725 may be inflated or expanded.

As illustrated in FIG. 7, the filling of the filler member 725 in the absence of reduced pressure to the space 728 may result in the dressing 702 expanding above the epidermis 713 of the patient that surrounds the tissue site 701. This expansion of the dressing 702 assists in applying a biasing force, represented by arrows 772, to the tissue site 701. The inflation of the filler member 725 beneath the cover 710 results in no reduced pressure being needed to encourage granulation. In this particular embodiment, fluid is removed from the dressing 702 without reduced pressure as well.

Figure 8:
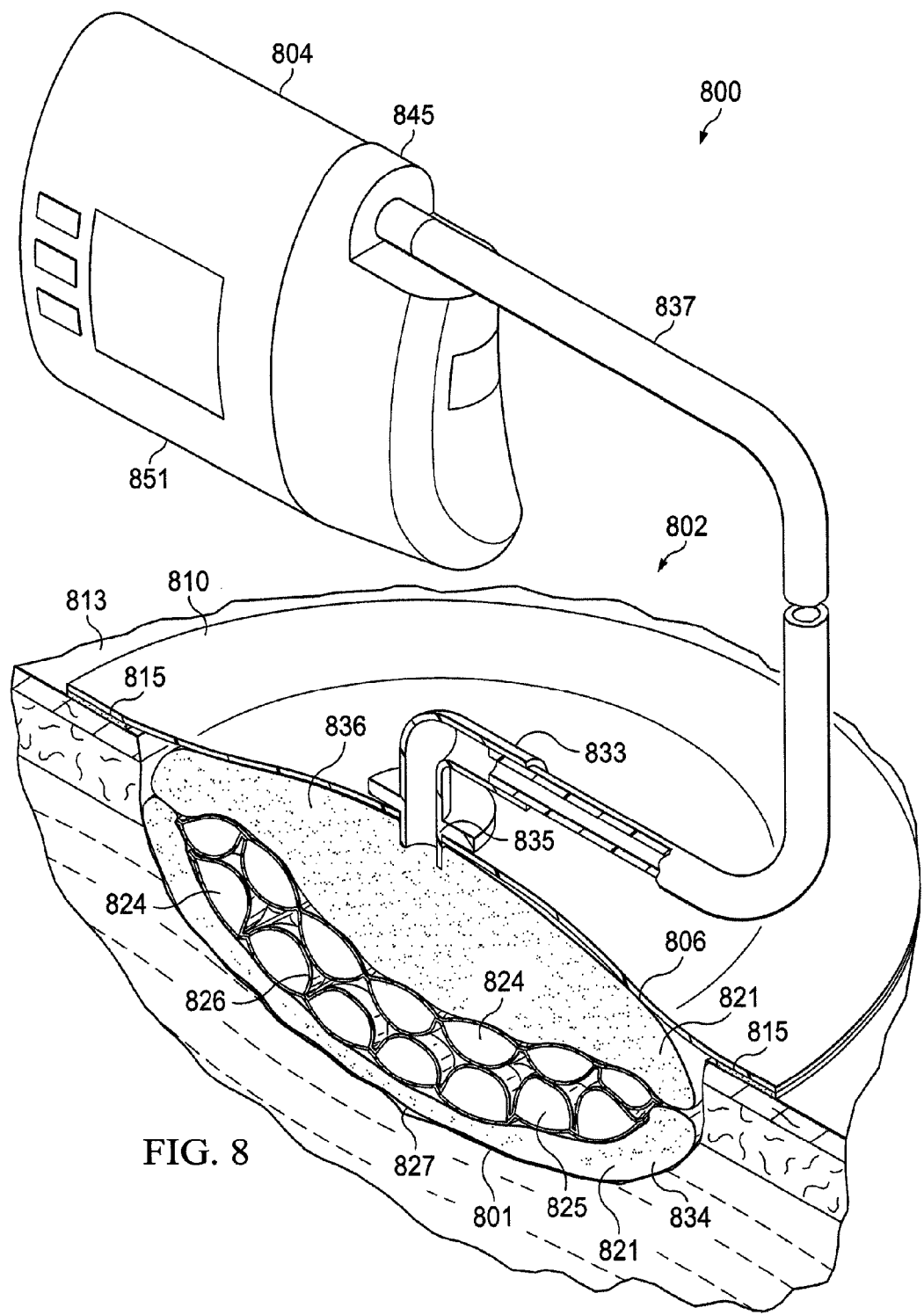
FIG. 8 illustrates a partially cross-sectional, perspective view of a tissue treatment system according to an illustrative embodiment, the tissue treatment system having a pre-inflated filler member.
Figure 9:
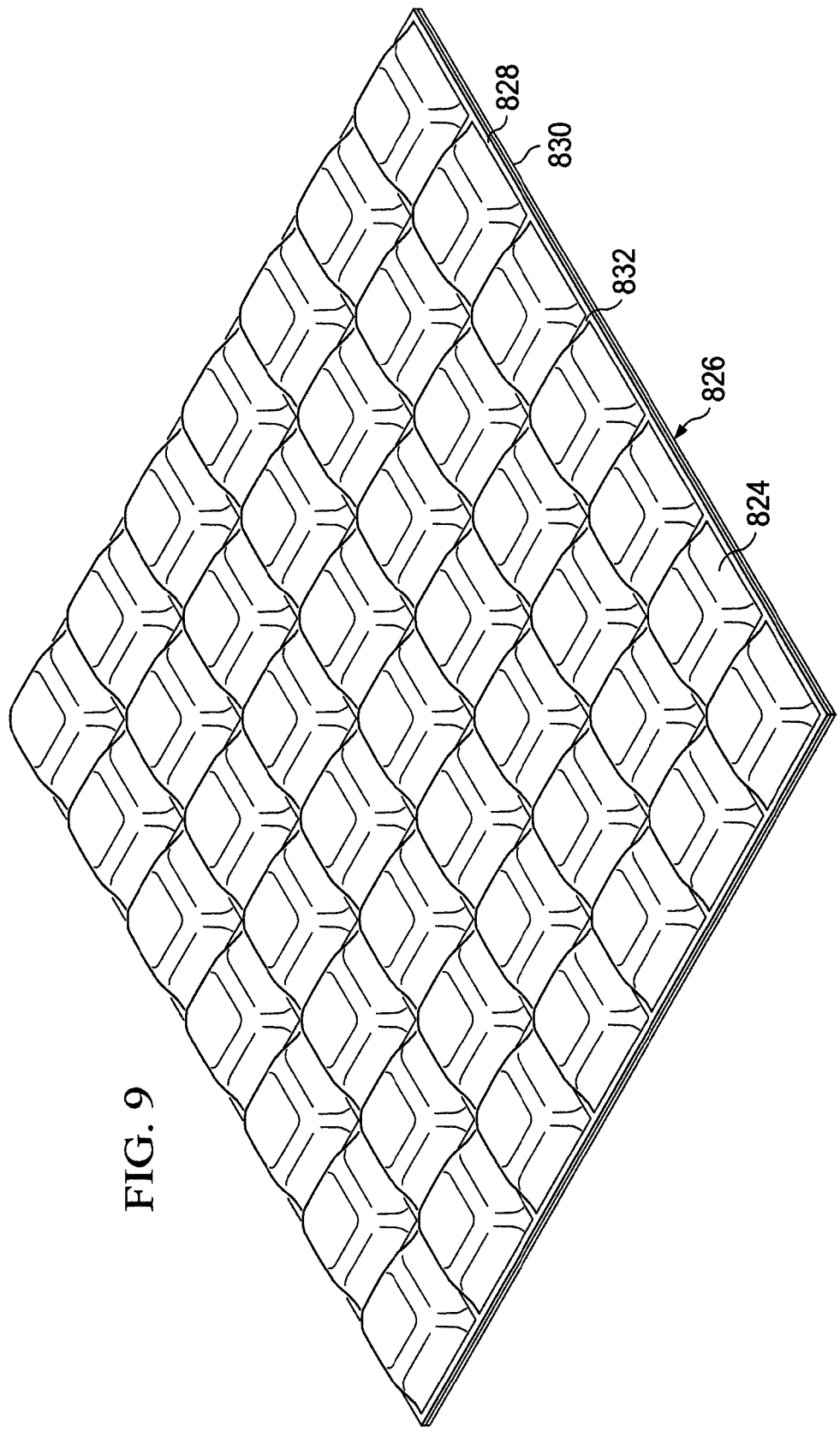
FIG. 9 illustrates a perspective view of the pre-inflated filler member of FIG. 8.
Figure 10:
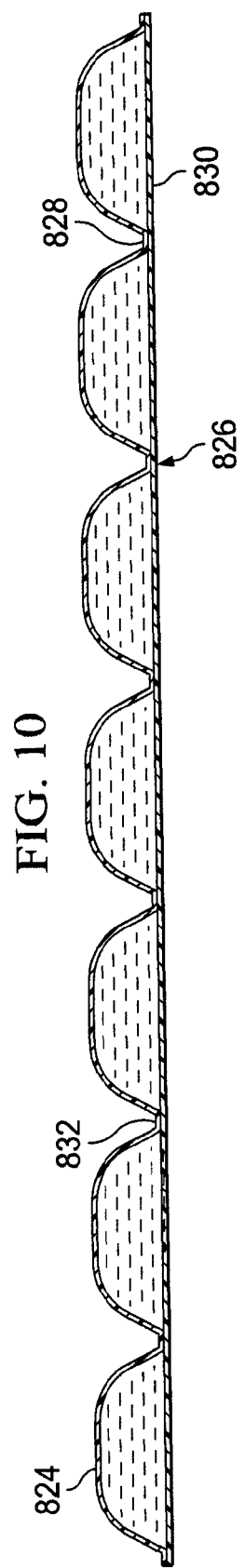
FIG. 10 illustrates a cross-sectional side view of the pre-inflated filler member of FIG. 9 taken at 10-10.

Referring to FIGS. 8-10, an illustrative embodiment of a tissue treatment system 800 for treating a tissue site 801 on a patient includes a dressing 802 placed proximate to the tissue site 801 and a therapy unit 804 fluidly coupled to the dressing 802. The dressing 802 is configured to promote the growth of new tissue at the tissue site 801 and includes a wound healing apparatus 806 positioned adjacent to or, in some embodiments, in contact with the tissue site 801. The dressing 802 may further include a cover or drape 810 positioned over the wound healing apparatus 806 to secure the wound healing apparatus 806 at the tissue site 801 and to seal a space that is beneath the cover and is at least partially occupied by the wound healing apparatus 806. In one embodiment, the drape 810 extends beyond a perimeter of the tissue site 801 and is placed either in contact with or otherwise in proximity to a patient's epidermis 813 to create a fluid seal between the drape 810 and the epidermis 813. The drape 810 may include an adhesive 815 or bonding agent to secure the drape 810 to the epidermis 813. In one embodiment, the adhesive 815 may be used to create a seal between the drape 810 and the epidermis 813 to prevent leakage of reduced pressure from the tissue site 801. In another embodiment, a seal layer (not shown) such as, for example, a hydrogel, hydrocolloid (for example as supplied by Avery or 3M), silicone gel (for example as supplied by Dowcoming, Wacker, or NuSil), hot-melt glue (for example as supplied by Plasto, Adhesive Research, or Avery), or other material may be disposed between the drape 810 and the epidermis 813 to augment or substitute for the sealing properties of the adhesive 815.

The wound healing apparatus 806 may include a manifold 821 and a filler member 825. In one embodiment, the wound healing apparatus 806 includes a porous foam and having a plurality of interconnected cells or pores that act as flow channels. The porous foam may be a polyurethane, open-cell, reticulated foam such as GranuFoam® material manufactured by Kinetic Concepts, Incorporated of San Antonio, Tex.

The filler member 825 of the reduced pressure apparatus 806 may be provided to occupy additional space or volume between the tissue site 801 and the cover 810 and may also be provided to better facilitate the application of a positive force to the tissue site 801 in order to encourage granulation and new tissue growth. In the embodiment illustrated in FIGS. 8-10, the filler member 825 is a pre-filled bladder or other container that is positioned between the tissue site 801 and the cover 810. The filler member 825 includes at least one chamber 824 sealingly enclosed by chamber walls 826. The chamber 824 retains a fluid that in one embodiment may be a gas such as air. The pressure of the fluid within the chamber 824 may be greater than or equal to ambient pressure. If the chamber walls 826 are elastically deformed, the fluid is most likely at a pressure slightly greater than ambient pressure. If the chamber walls 826 are not elastically deformed, the pressure of the fluid may be about the same as ambient.

In the embodiment illustrated in FIGS. 9 and 10, the chamber walls 826 of the filler member 825 include a first wall 828 joined to a second wall 830 to form the chamber 824. In this embodiment, the filler member 825 includes a plurality of chambers 824, each chamber 824 being connected to an adjacent chamber at a sealing joint 832. The sealing joint 832 is the location at which the first and second walls 828, 830 are sealed together, and this sealing process may be accomplished by heat bonding, adhesive bonding, ultrasonic welding, or any other process capable of connecting the walls 828, 830 together. The process chosen to bond the walls 828, 830 may vary depending on the material property of the walls 828, 830. The sealing joint 832 acts as a hinge between adjacent chambers 824, thereby allowing rotational movement of one chamber 824 relative to another. As an alternative to the sealing joint 832 forming a hinged connection between adjacent chambers 824, a plurality of chambers 824 may be adhered or otherwise attached to a flexible membrane or substrate such that a hinged configuration is provided between adjacent chambers 824.

Although the filler member 825 has been described as including first wall 828 and second wall 830, it should be noted that each chamber 825 may constructed from individual walls separate from the walls that form adjacent chambers. In addition, the number of walls associated with the filler member 825 or each chamber may vary depending on the desired shape of each chamber or the filler member. For example, a chamber that is formed in the shape of an octahedron may include eight walls. Alternatively, a spherical chamber may only include a single wall.

The walls 828, 830 of the filler member 825 may be made from any flexible material that is capable of maintaining a substantially sealed chamber. Examples of suitable materials may include polyurethanes, thermoplastic elastomers, silicone elastomers and other elastomeric polymers such as poly-epichlorohydrin, butyls (including halogenated forms), or polyether block amine copolymers (PEBAX), and thin flexible films, such as polyolefines, copolyesters, and polyamides.

The manifold 821 and filler member 825 may work together to encourage tissue growth in the presence of a positive force or pressure. In one-embodiment, the manifold 821 may include at least one granulation-promoting surface 827 that is capable of contacting the tissue site 801. The granulation-promoting surface 827 is capable of inducing micro-stresses and micro-strain at the tissue site 801 when the granulation-promoting surface 827 contacts the tissue site 801. For example, if the manifold 821 is a reticulated porous foam that includes a plurality of interconnected cells formed by struts or cell walls, the struts of the reticulated foam may be capable of inducing micro-stresses and micro-strains when the struts are pressed against or into the tissue. By sealing the manifold 821 and filler member 825 proximate the tissue site 801 with the cover 810, the presence of the filler member 825 within the sealed space beneath the cover 810 assists in directing a force on the manifold 821 at least in the direction of the tissue site 801. This force is capable of generating the required micro-stresses and micro-strains where the tissue contacts the granulation-promoting surface 827.

In one embodiment, the cover 810 may be placed over the manifold 821 and filler member 825 such that the filler member 825 is somewhat compressed as the cover 810 is attached to the patient. This compression of the filler member 825 assists in amplifying the force applied to the manifold 821 and thus the tissue site 801. Although not required, the cover 810 may be formed from a material that is elastically deformed as the cover 810 is applied. Examples of suitable cover materials may include polyurethanes, thermoplastic elastomers, silicone elastomers and other elastomeric polymers such as poly-epichlorohydrin, butyls (including halogenated forms), or polyether block amine copolymers (PEBAX), and thin flexible films, such as polyolefines, copolyesters, and polyamides.

In FIG. 8, the filler member 825 is positioned between a first portion 834 and a second portion 836 of the manifold 821. A pressure interface 833 is fluidly coupled to the wound healing apparatus 806 and the cover 810. In one embodiment, the interface 833 may be positioned adjacent to or coupled to the cover 810 to provide fluid access to the wound healing apparatus 806. The cover 810 includes an aperture 835 for providing fluid access to the interface 833. A conduit 837 fluidly couples the therapy unit 804 and the interface 833. The interface 833 is capable of allowing reduced pressure to be delivered to the tissue site 801 when it is desired to remove fluid from the tissue site 801 under the influence of reduced pressure.

In one embodiment, the therapy unit 804 includes a fluid containment member 845 in fluid communication with a reduced pressure source 851. Liquids or exudates communicated from the wound healing apparatus 806 through the conduit 837 are removed from the conduit 837 and retained within the containment member 845. In the embodiment illustrated in FIG. 8, the fluid containment member 845 is a collection canister that includes a chamber for collecting fluids from the tissue site 801. The fluid containment member 845 alternatively could be an absorbent material or any other container, device, or material that is capable of collecting fluid.

Referring still to FIG. 8, the reduced pressure source 851 may be one or more electrically-driven vacuum pumps. In another implementation, the reduced pressure source 851 may instead be one or more manually-actuated or manually-charged pumps that do not require electrical power. The reduced pressure source 851 instead may be any other type of pump, or alternatively a wall suction port or air delivery port such as those available in hospitals and other medical facilities. The reduced pressure source 851 may be housed within or used in conjunction with the therapy unit 804, which may also contain sensors, processing units, alarm indicators, memory, databases, software, display units, and user interfaces 861 that further facilitate the application of reduced pressure treatment to the tissue site 801. In one example, pressure-detection sensors (not shown) may be disposed at or near the reduced pressure source 851. The pressure-detection sensors may receive pressure data from the interface 833 via lumens in the conduit 837 that are dedicated to delivering reduced pressure data to the pressure-detection sensors. The pressure-detection sensors may communicate with a processing unit that monitors and controls the reduced pressure that is delivered by the reduced pressure source 851.

To use the tissue treatment system 800, a caregiver places the first portion 834 of the manifold 821 in contact with the tissue site 801 such that the granulation-promoting surface 827 is in contact with the tissue site 801. The filler member 825 is then positioned above the first portion 834, and preferably the amount of filler member 825 is adjusted to substantially fill the space that will be beneath the cover 810. The filler member 825 may be trimmed along the sealing joints 832 or through the chambers 824 to re-size the filler member 825 to an appropriate size. In the embodiment illustrated in FIG. 8, a single-piece filler member 825 is folded in half to more adequately fill the space. Alternatively, multiple pieces of the filler member 825 may be positioned to substantially fill the space. In one embodiment, enough of the filler member 825 is added to allow the filler member 825 to be substantially level with the epidermis 813 surrounding the tissue site 801. After placement of the filler member 825, the second portion 836 of the manifold 821 is positioned above the filler member 825, and then the cover 810 is positioned over the second portion 836. The cover 810 is secured to the epidermis 813 surrounding the tissue site 801, and the pressure interface 833 is positioned in contact with the cover 810 and in communication with the aperture 835. The reduced pressure source 851 is fluidly connected to the pressure interface 833.

As reduced pressure is applied to the space beneath the cover 810, air and other fluids removed from the space cause the cover 810 to compress toward the tissue site 801. This compression enhances the force exerted on the tissue site 801 by the granulation-promoting surface 827, and aids in the formation of granulation tissue. As exudate and other fluids are produced by the tissue site 801, the presence of the manifold 821 below and above the filler member 825 assists in channeling the fluids around the filler member 825 and into the fluid containment member 845.

While the tissue treatment system 800 of FIG. 8 is described as having a two-piece manifold system surrounding the filler member, the manifold could be a one-piece manifold that encases the filler member. Alternatively, as previously described in relation to FIG. 7, the manifold may be omitted and a filler member used that includes a granulation-promoting surface. Similarly, many fluid handling and storage alternatives are possible for the tissue treatment system 800. In a similar manner to those system described previously herein, the collection canister that is remotely located from the tissue site may instead be an absorbent material. The absorbent material may be provided as a layer of the dressing as shown in FIG. 4, or may be located external to the dressing as shown in FIGS. 5-7.

The multi-chambered filler member 825 described herein is pre-inflated and sealed such that the fluid within each chamber is trapped. While it may be preferred in the embodiment illustrated in FIG. 8 to use a pre-inflated filler member, it should be noted that the fillable and expandable filler members described herein and illustrated in FIGS. 1-7 may also be multi-chambered similar to filler member 810. In other words, it is contemplated that a multi-chambered filler member could be connected to a positive pressure source such that the delivery of fluid to the chambers under positive pressure may be controlled following placement of the filler member in proximity to the tissue site.

The tissue treatment systems described herein allow the use of a reduced pressure treatment protocol that uses less reduced pressure (i.e. higher absolute pressures) than traditional protocols. By increasing the granulation-inducing microstrains and microstresses using positive forces and positive pressures, the amount of reduced pressure needed for treatment is greatly reduced. In fact, testing has shown that a pressure of −75 mm Hg, coupled with a positive pressure provided by either an inflatable or pre-inflated bladder, achieves an interface-pressure equivalent (the pressure measured at the interface of the granulation-promoting surface and the tissue site) of −125 mm Hg.

The systems described herein have the ability to manage fluid and interfacial pressures independently. This is particularly useful in intermittent mode where a caregiver can maintain constant fluid management (e.g. removal) while alternating the application of microstrain on the tissue site. This also may be more beneficial for pain management in that the effect of transient strains my be reduced by managing the application of the positive and negative pressures independently. Finally, these methods result in a simpler system with lower energy requirements.

The separation of fluid removal and microstrain induction may also be beneficial when it is not desirable to draw together the perimeter of a wound or tissue site. In traditional reduced pressure treatment, the application of higher amounts of reduced pressure to dressings promoted closure by primary intention by drawing together the edges or perimeter of the wound. However, this is not always advantageous, especially when the wound is to a joint or articulation point. In these areas of articulation, the contraction of tissue may lead to impinged movement, which may cause secondary problems for the patient or the need for painful physiotherapy to break down these tissue formations to restore movement. It may beneficial in these circumstances to heal the wound by secondary or tertiary (delayed primary) intention as is commonly used in reconstructive surgery. The tissue treatment systems described herein allow the benefit of reduced pressure treatment to be applied to a wound, yet the inflatable or pre-inflated bladder resists the collapse of the wound perimeter inward and thus constriction of the surrounding tissue.

While many of the systems described herein have been illustrated in use with tissue sites or wounds that are at or near the epidermis of a patient, the systems and methods may similarly be used to treat subcutaneous tissue sites, tunnel wounds, or other undermined areas of tissue. With these types of wounds or tissue sites, accessibility may be limited, thereby making placement and removal of traditional foams and manifolds more difficult. The ability of the bladders described herein to be deflated upon installation and removal would ease the process of applying treatment to these difficult-to-access wounds and tissue sites.

While many of the tissue treatment systems described herein include the use of negative pressure in conjunction with the application of a positive pressure or force, the use of absorbent materials for passive fluid removal may assist in completely eliminating the need for reduced pressure. In such a system, fluid may be removed passively from the wound and stored in an absorbent layer, while a positive pressure or force is used to create microstrains at the tissue site.

While many of the tissue treatment systems described herein may include a separate cover member or drape to secure and seal the filler member and any granulation-promoting surfaces or material at the tissue site, the cover member or drape may be integrally combined with the filler member to secure or seal these components at the tissue site. For example, in one embodiment, the cover member may be an integral portion of the filler member that is capable of being secured to an epidermis of the patient such that the interior chamber of the filler member and any granulation-promoting material is sealed within a space beneath the cover member at the tissue site.

It should be apparent from the foregoing that an invention having significant advantages has been provided. While the invention is shown in only a few of its forms, it is not just limited but is susceptible to various changes and modifications without departing from the spirit thereof.

We claim:

1. A wound healing system for promoting healing of a wound of a patient, the system comprising:
    a pump having an inlet and an exhaust, the inlet of the pump having a reduced pressure that is less than a reference pressure and the exhaust having a positive pressure that is greater than the reference pressure;
    a granulation-promoting material adapted to be positioned in contact with the wound and fluidly connected to the inlet of the pump;
    a filler member having an interior chamber fluidly connected to the exhaust of the pump; and
    a cover member adapted to be positioned over the filler member to secure the filler member at the wound.

2. The wound healing system of claim 1, wherein the filler member comprises a granulation-promoting surface.

3. The wound healing system of claim 1, wherein the granulation-promoting material is adapted to be positioned between the filler member and the wound to induce microstrain at the wound when the filler member is expanded.

4. The wound healing system of claim 1, wherein the granulation-promoting material is a polyurethane, open-cell, reticulated foam.

5. The wound healing system of claim 1, wherein the filler member is embedded within and surrounded by the granulation-promoting material.

6. The wound healing system of claim 1, wherein:
    the granulation-promoting material includes at least a first portion and a second portion;
    the first portion is adapted to be positioned between the filler member and the wound; and
    the second portion is adapted to be positioned between the filler member and the cover member.

7. The wound healing system of claim 1 further comprising a fluid containment member fluidly connected between the inlet of the pump and the wound to collect exudate from the wound.

8. The wound healing system of claim 7, wherein the fluid containment member is a fluid collection canister.

9. The wound healing system of claim 7, wherein the fluid containment member is an absorbent layer positioned beneath the cover member.

10. The wound healing system of claim 7, wherein the fluid containment member is an absorbent-containing fluid pouch positioned outside of the cover member.

11. The wound healing system of claim 1, wherein the interior chamber of the filler member further comprises a plurality of interior chambers fluidly connected to the exhaust of the pump.

12. A wound healing system for promoting healing of a wound of a patient, the system comprising:
    a pump having an inlet and an exhaust, the inlet of the pump having a reduced pressure that is less than a reference pressure and the exhaust having a positive pressure that is greater than the reference pressure;
    a granulation-promoting material adapted to be positioned in contact with the wound and fluidly connected to the inlet of the pump; and
    a filler member having an interior chamber fluidly connected to the exhaust of the pump, the filler member further comprising a cover member capable of sealing the granulation-promoting material and the interior chamber within a space beneath the cover member at the wound, wherein the filler member is embedded within and surrounded by the granulation-promoting material.

* * * * *